United States Patent [19]

Harrison

[11] 4,257,984
[45] Mar. 24, 1981

[54] MONOTERTIARYMONOSECONDARYDI-PRIMARYTETRAMINE AND MONOTERTIARYMONOSECONDARYDINITRILODIAMINES

[75] Inventor: Stuart A. Harrison, Minneapolis, Minn.

[73] Assignee: Henkel Corporation, Minneapolis, Minn.

[21] Appl. No.: 784,381

[22] Filed: Apr. 4, 1977

[51] Int. Cl.³ .................... C07C 87/20; C07C 87/24; C07C 87/28; C07C 87/50
[52] U.S. Cl. ............................. 564/336; 260/32.6 N; 260/32.6 PQ; 260/37 FP; 260/37 P; 260/465 E; 260/465.5 R; 528/422; 564/385; 564/420; 564/490; 564/512
[58] Field of Search ......... 260/583 H, 583 P, 570.5 P, 260/2 N, 47 EN, 576, 577, 583 K

[56] References Cited

U.S. PATENT DOCUMENTS

| | | | |
|---|---|---|---|
| 2,638,450 | 5/1953 | White et al. | 260/583 P X |
| 2,984,687 | 5/1961 | Esmay et al. | 260/577 |
| 3,280,074 | 10/1966 | McCaleb et al. | 260/47 EN |
| 3,337,609 | 8/1967 | Williamson et al. | 260/47 EN X |
| 3,352,813 | 11/1967 | Hayes | 260/47 EN X |
| 3,364,248 | 1/1968 | Miller et al. | 260/47 EN X |
| 3,519,582 | 7/1970 | Clelford et al. | 260/2 N X |
| 3,527,804 | 9/1970 | Cyba | 260/570.5 P X |
| 3,658,728 | 4/1972 | Hoffmann et al. | 260/2 N |
| 3,694,409 | 9/1972 | Millar et al. | 260/47 EN |
| 3,962,337 | 6/1976 | Drake | 260/583 K |
| 4,044,053 | 8/1977 | Brennan et al. | 260/583 P |

FOREIGN PATENT DOCUMENTS 711654 7/1954 United Kingdom ................ 260/583 P

OTHER PUBLICATIONS

Monsanto, "French Patents Abstracts", 7, No. 27, p. 5:9, (1967).

*Primary Examiner*—John Doll
*Attorney, Agent, or Firm*—Forrest L. Collins; Patrick J. Span

[57] ABSTRACT

The present invention relates to epoxy resin compositions and in particular to curing agents for such resin compositions. The present invention thus embraces monotertiarymonosecondarydiprimarytetramines and the precursor from which this amine is manufactured namely monotertiarymonosecondarydinitrilodiamines.

24 Claims, No Drawings

MONOTERTIARYMONOSECONDARYDI-PRIMARYTETRAMINE AND MONOTERTIARYMONOSECONDARYDINI-TRILODIAMINES

BACKGROUND OF THE INVENTION

1. Field of the Invention

The present invention describes compositions useful in preparing coatings for substrates such as metals, plastic, glass, wood and other such materials.

2. Description of the Art

Epoxy resins having more than one epoxide group per mole of the resin are known in the art to form hard insoluble and infusible products. It is also known that compounds having primary or secondary amine structures will react with epoxy resins. Polyamines, that is, compounds having more than one amine group are utilized to cure such epoxy resins.

U.S. Pat. No. 3,280,074 issued Oct. 18, 1966 to McCaleb et al. states that complex amines having a monotertiarydiprimary structure may be used as curing agents for the epoxy resins described above.

While the amines described in the McCaleb et al. patent function well for their intended purpose it cannot be said that these materials could not be improved upon. Among the areas of improvement that are encompassed by the present invention include the observation that the processing of the materials in the McCaleb patent require large amounts of hydrogenation catalysts which have been found to be deactivated in short order by the acetic or phosphoric acid used in preparing the final amine product therein. The acid is needed to ensure that the secondary amine will react with the nitrile compound.

To counteract the effect of the acid deactivation of the hydrogenation catalyst it has been proposed to neutralize the acid with a caustic material. This, however, results in salt formation and a second step must be employed to remove the salt by washing with copious amounts of water. It is also observed that the water deactivates the hydrogenation catalyst when present at any substantial level during the hydrogenation reaction. Thus, while the acid may be neutralized and the resulting salts washed out of the reaction mixture it is necessary to employ yet a further step, usually evaporation, to remove the water from the reaction mixture to avoid a second source of catalyst deactivation.

It has been found in the present invention that the monotertiarymonosecondarydiprimarytetramines (also referred to as tetram) and the precursor monotertiarymonosecondarydinitrilodiamines require no acid utilization in their preparation and thus the neutralization, water washing and subsequent water removal are avoided in forming the claimed compounds of the present invention.

A second advantage in avoiding the acid used in the prior art is that a single solvent may be employed, usually methanol, throughout the reaction process to form the tetram. Therefore while the process of McCaleb et al also uses methanol that solvent must be stripped out during the water washing and recovered for subsequent use whereas in the present invention the methanol need not be reclaimed until the final step of tetram formation. It must be remembered that in McCaleb et al. that the solvent would also be reclaimed following the final step thus the present invention requires only one purification step for reuse of the solvent. Therefore the amount of valuable product which is carried off and lost with the solvent can be twice as great in McCaleb et al than in the present invention. Further, the solvent which can be lost in the atmosphere due to two recovery steps is greater than the one step solvent recovery in the present invention.

It has also been observed that the tetrams of the present invention have a longer pot life and form harder coatings upon curing the epoxy resins than do the compositions of McCaleb et al. While the secondary amine structure in McCaleb et al. causes processing difficulties and is eventually obliterated to form the end polyamine compound therein the present invention retains a secondary amine group which causes greater crosslinking with the epoxy resin. Pot life refers to the duration of time between the mixing of the tetram and the epoxy resin and the point at which the mixture becomes too viscous to apply to the substrate. It is universally desired that the pot life of any given coating agent be sufficiently long to avoid hardening of the mixture in the mixing vessel or pot. While the compounds of the present invention do exhibit long pot life they are particularly advantageous in that they cure quickly upon application to the substrate. Moreover, the coating formed by the tetram of the present invention in combination with the epoxy resin does not carbonate, i.e. turn white upon application to the substrate. This is particularily valuable when working with unpigmented coatings requiring a clear finish on the substrate. In addition, the non-carbonating feature of the tetram and epoxy resin cured mixture provides greater strength than prior art epoxy resin compositions which do undergo carbonation in curing.

It has also been observed that the tetrams of the present invention are liquids at room temperature and thus do not require the expenditure of costly energy to melt the tetram prior to combination with the epoxy resin. Moreover, the tetrams of the present invention are not only liquid but are of sufficiently low viscosity that mixing is easily accomplished upon combination with the epoxy resin in the pot.

It has also been found that the precursor of the tetram namely the monotertiarymonosecondarydinitrilodiamine is itself a preferred curing agent for several resin compositions. Such resin compositions include the reaction product of the dinitrilodiamine with olefins (alkenyl) to give substituted fatty acid amides in the presence of sulfuric acid catalyst. The dinitrilodiamines of the present invention may also be reacted with water in the presence of acid catalysts to give the corresponding fatty diamides and with hydrogen sulfide to give fatty dithioldiamide compounds. Thus the dinitrilodiamines are useful for the preparation of a host of compounds including the tetrams of the present invention.

Throughout the specification and claims percentages and ratios are by weight and temperatures are in degrees Celsius unless otherwise indicated.

SUMMARY OF THE INVENTION

The present invention embodies a process for the preparation of a nonlinear monotertiarymonosecondarydinitrilodiamine including the steps of:

(a) reacting a primary amine of the formula

wherein $R^1$ is an organic moiety of from 4 to 40 carbon atoms with a nitrile of the formula

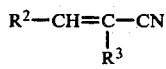

wherein $R^2$ is selected from the group consisting of alkyl and alkenyl radicals having from 1 to 40 carbon atoms, hydrogen, phenyl, phenylalkyl, alkylphenyl derivatives and mixtures thereof; and $R^3$ is hydrogen or methyl and mixtures thereof to yield

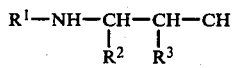

(b) reducing the compound prepared in (a) with hydrogen to form a compound of the formula

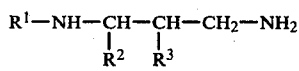

wherein $R^1$, $R^2$, and $R^3$ are defined above;

(c) then reacting the reduced compound of (b) with a second portion of a nitrile described in (a) to form

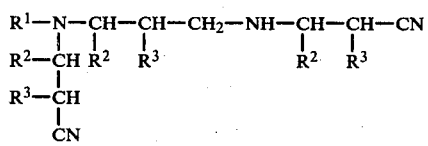

wherein $R^1$, $R^2$, and $R^3$ are as defined above.

The present invention also embodies the process for the production of a non-linear monotertiarymonosecondarydiprimarytetramine by following steps (a), (b), and (c) above; and, (d) then reducing the compounds described in (c) with hydrogen to form

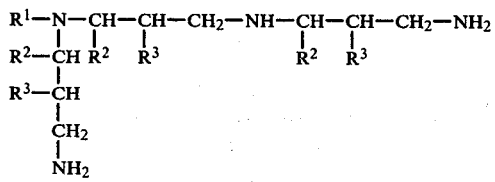

wherein $R^1$, $R^2$, and $R^3$ are as defined above.

The present invention further embodies the compounds obtained from both of the processes described above, namely the monotertiarymonosecondarydinitrilodiamine of (c) above and the monotertiarymonosecondarydiprimarytetramine of (d) shown above.

The present invention also embodies a curable composition of an epoxy resin having 1,2-epoxide groups and a monotertiarymonosecondarydiprimarytetramine in an amount sufficient to cure the epoxy resin to a hard, insoluble product as well as the process of carrying out the above-mentioned reaction.

DETAILED DESCRIPTION OF THE INVENTION

The present invention as previously stated relates to the production and utilization of non-linear monotertiarymonosecondarydinitrilodiamines and monotertiarymonosecondarydiprimarytetramines for resin coatings. The non-linear nature of the claimed compounds arises from the fact that the tertiary nitrogen is attached to the organic moiety $R^1$ such as an alkyl, alkenyl, phenyl, alkylphenyl or phenylalkyl (where the alkyl residue in either aromatic radical is preferably $C_1$–$C_4$) which is linear thus the primary nitrogens (or nitrile) are in a nonlinear relationship to one another.

The first aspect to be discussed in the present invention is that of the preparation of the dinitrilodiamine compound and the tetram. The non-linear monotertiarymonosecondarydinitrilodiamine is basically prepared by reacting a primary amine having the formula:

$$R^1NH_2$$

wherein $R^1$ is an organic moiety of from 4 to 40 carbon atoms preferably an alkyl or alkenyl radical having from about 10 to about 22 carbon atoms and most preferably having an even number of carbon atoms from 12 to 18 with a nitrile of the formula as shown in the summary of the invention wherein $R^2$ is an alkyl or alkenyl radical having from 1 to 40 carbon atoms, hydrogen, phenyl or alkyl(preferably $C_1$–$C_4$ alkyl)phenyl and  is hydrogen or methyl to form the previously shown adduct. In the reaction $R^2$ is preferably hydrogen although lower alkyl or alkenyl (olefin) radicals having from 1 to 4 carbon atoms maybe effectively used. In the most preferred circumstance both $R^2$ and $R^3$ are hydrogen.

As noted previously no catalyst such as the acid required by prior art practices is needed to form the adduct. The solvent utilized throughout the processing of the present invention is preferably a lower alkanol such as methanol, ethanol, or propanol, although ethers, such as diethyl ether or tetrahydrofuran may be employed. Most preferably, however, the solvent for cost and processing reasons is methanol. Preferably the solvent is present in a weight ratio to the total reactants in the process at a level of from about 5% to 100%. This solvent level is conveniently maintained throughout the remaining processing steps to the final formation of the tetram.

Conveniently the primary amine, the solvent and the nitrile are placed in an enclosed vessel and stirred and heated under reflux for a period of from about 1 to 3 hours at which time the reaction is complete. This is in contrast to the corresponding reaction in McCaleb et al where the initial period of stirring and refluxing the reaction mixture is followed by allowing the product to stand at 47° C. for 40 hours. The reaction mixture is thereafter hydrogenated preferably using a hydrogenation catalyst such as Raney nickel, Raney cobalt, or platinum to form the monosecondarymonoprimarydiamine as shown in (b). Where the nitrile is not completely consumed in the addition reaction it is desirable to flush the excess out of the vessel prior to the hydrogenation to avoid undesirable by-products.

The diamine so formed is then reacted with an additional portion of the nitrile which is added over a period of about one hour by means of a dropping funnel to the diamine. Inasmuch as the reaction is exothermic, little energy need be applied. However, the temperature of the reaction vessel should be maintained between about 30° and 90° C. to ensure substantial completion of the reaction. Following complete addition of the nitrile this reaction mixture is refluxed for from about 1 to 3 hours with an optimum refluxing temperature of about 80° C. It is noted than in either of the two nitrile addition reactions that the nitrile is used in the equivalent quantity needed to prepare the desired adduct. Conveniently where yield of the desired products is flexible the equivalent ratio may be between 0.7:1 to 2:1, most preferably 0.8:1 to 1.5:1 of the acrylonitrile to the amine.

Following the addition of the second portion of the nitrile, the compound shown in the Summary at (c) is obtained. At this point the production of the non-linear monotertiarymonosecondarydinitrilodiamine is complete and the solvent and any excess nitrile may be removed by distillation.

The formation of the non-linear monotertiarymonosecondarydiprimarytetramine is prepared by hydrogenating the corresponding dinitrilodiamine. The conditions for the hydrogenation are as previously noted preferably using a hydrogenation catalyst. Again, any excess nitrile should be removed prior to hydrogenation. The pressure for the hydrogenation in absolute units should not be less than 15,000 mm Hg and should be conducted at a temperature from about 60° C. to about 120° C. Preferably the hydrogenation conditions are such that the pressure is at least about 18,000 mm Hg absolute and from about 80° C. to about 110° C. It is preferred that during the hydrogenation reaction that ammonia be added to the reaction vessel to minimize the tendency of compound (b) to condense with itself and liberate ammonia gas. The total pressure requirements for the mixture of the compound (c), the hydrogen gas and the ammonia are generally required to be in the range of 18,000 mm to 24,000 mm Hg.

The tetrams so formed are then reacted with any convenient epoxy resin to form the curable coating compositions of the present invention. These epoxy resins may be both solid or liquid materials. It is of course, preferable that the epoxy resin be a liquid material to facilitate mixing and enhance pot life.

In general, the most commonly available epoxy resins are those which are the reaction products of epichlorohydrin and bis(parahydroxyphenyl) propane, "bisphenol A," such as are described in the McCaleb et al U.S. Pat. No. 3,280,074 incorporated herein by reference. Alternatively, "bisphenol F" which is bis(parahydroxyphenyl)methane may be utilized.

Other such epoxy resins are those which are the reaction product of epichlorohydrin and bis(parahydroxyphenyl) sulfone. Still another group of epoxy compounds which may be employed are the glycidyl esters of the polymeric fat acids. These glycidyl esters are obtained by reacting the polymeric fat acids with polyfunctional halohydrins such as epichlorohydrins. In addition, the glycidyl esters are also commercially available epoxide materials. The glycidyl esters of the polymeric fat acids are also useful in the present invention and are also described in the McCaleb et al. patent.

The polymeric fat acids are well known materials, commercially available, which are the products from the polymerization of unsaturated fatty acids to provide a mixture of dibasic and higher polymeric fat acids. The polymeric fat acids are those resulting from the polymerization of the drying or semidrying oils or the free acids or the simple aliphatic alcohol esters of such acids. Suitable drying or semi-drying oils include soybean, linseed, tung, perilla, oiticia, cottonseed, corn, sunflower, safflower, dehydrated castor oil and the like. The term "polymeric fat acids" as used herein and as understood in the art, is intended to include the polymerized mixture of acids which usually contain a predominant portion of dimer acids, a small quantity of trimer and higher polymeric fat acids and some residual monomers.

In general, the most readily available naturally occurring polyunsaturated acid available in large quantities is linoleic acid. Accordingly, it should be appreciated that polymeric fat acids will, as a practical matter, result from fatty acid mixtures that contain a preponderance of linoleic acid and will thus generally be composed largely of dimerized linoleic acid. However, polymerized fatty acids may be prepared from the naturally occurring fatty acids having from 8 to 22, and preferably 16 to 20, carbon atoms. Illustrative thereof are oleic, linolenic, palmitoleic, and the like.

Other types of epoxy resins which may be cured with the present products and which are commercially available epoxy materials are the polyglycidyl ethers of tetraphenols which have two hydroxy aryl groups at each end of an aliphatic hydrocarbon chain. These polyglycidyl ethers are obtained by reacting the tetraphenols with polyfunctional halohydrins such as epichlorohydrin. The tetraphenols used in preparing the polyglycidyl ethers are a known class of compounds readily obtained by condensing the appropriate dialdehyde with the desired phenol. Typical tetraphenols useful in the preparation of these epoxy resins are the alpha, omega, omega-tetrakis (hydroxyphenol) alkanes, such as 1,1,2,2-tetrakis(hydroxyphenol) ethane, 1,1,4,4-tetrakis(hydroxyphenol) butane, 1,1,4,4-tetrakis(hydroxyphenol) - 2 -ethylbutane and the like. The epoxy resin reaction product of the epichlorohydrin and tetraphenol is also shown in the McCaleb et al. patent with the appropriate limitations shown therein.

Still another group of epoxide materials are the epoxidized novolac resins. Such resins are well-known substances and readily available commercially as evidenced in McCaleb et al.

In general, these resins are obtained by epoxidation of the well-known novolac resins. The novolac resins, as is known in the art, are produced by condensing the phenol with an aldehyde in the presence of an acid catalyst. Although novolac resins from formaldehyde are generally employed, novolac resins from other aldehydes such as, for example, acetaldehyde, chloral, butyraldehyde, furfural, and the like, may also be used. The alkyl groups, if present, may have a straight or a branched chain. Illustrative of the alkylphenol from which the novolac resins may be derived are cresol, butylphenol, tertiary butylphenol, tertiary amylphenol, hexylphenol, 2-ethylhexylphenol, nonylphenol, decylphenol, dodecylphenol, and the like. It is generally preferred, but not essential, that the alkyl substituent be in the para position in the phenolic nucleus. However, novolac resins in which the alkyl groups are in the ortho position have been prepared.

The epoxidized novolac resin is formed in the well-known manner by adding the novolac resin to the epichlorohydrin and then adding an alkali metal hydroxide to the mixture so as to effect the desired condensation reaction.

In addition, other epoxy resins which may be cured with the curing agent of the present invention are the glycidyl ethers of the polyalkylene glycols, epoxidized olefins such as epoxidized polybutadiene and epoxidized cyclohexanes.

In general, the epoxy resins may be described as those having terminal epoxide groups.

In addition, the epoxy resins may be characterized further by reference to their epoxy equivalent weight, the epoxy equivalent weight of pure epoxy resin being the mean molecular weight of the resins divided by the mean number of epoxy radicals per molecule, or, in any case, the number of grams of epoxy resin equivalent to one epoxy group or one gram equivalent of epoxide. The epoxy resinous materials employed in this invention have an epoxy equivalent weight of from about 140 to about 2,000, preferably from about 140 to 300.

Liquid modifiers such as triphenyl phosphite (Mod-Epox), a tertiary amine (DMP30), nonyl phenol, and flow control agents such as silicone resins and oils may be used to achieve quicker curing or smoother films when dried under adverse conditions. Liquid plasticizers such as dibutyl phthalate may be added. The addition of judicious amounts of triphenyl phosphite or fluid plasticizers would reduce viscosity further to facilitate handling. Small amounts of solvents may be used to secure even lower viscosity, but of course, the combination would not then be solvent free.

Solid modifiers may be used such as pigments and fillers normally used in paints, or sand which might be added to produce trowelling concrete toppings or floor coatings. Treated clays and amorphous silica may be used to secure non-sagging thick coatings for vertical surfaces.

The following are examples of the present invention:

EXAMPLE I

Ten equivalents of a commercially distilled tallow primary amine (2570 grams) is added to 260 grams of methanol and reacted with 10 equivalents of acrylonitrile. The mixture is stirred and heated under reflux for about 2½ hours. The resultant compound having the structure (a cyanoethylamine derivative) shown in the Summary at (a) where $R^1$ is the fatty residue of the primary amine and $R^2$ and $R^3$ are both hydrogen is formed. This compound is then reduced with hydrogen over 457 grams of (62% solids) methanol wet Raney nickel. To accomplish the reduction the reaction flask is first charged with ammonia to a pressure of 4,000 mm Hg at 20° C. and then the hydrogen pressure is established such that the total pressure at 65° C. is 20,000 mm Hg. The resultant compound following hydrogenation is the monosecondarymonoprimarydiamine shown at (b).

The ammonia and the hydrogen are then flushed from the vessel with an inert gas such as nitrogen. The Raney nickel may be filtered out at this point or retained in the mixture. A second portion of acrylonitrile is then reacted in a one mole excess to the monosecondarymonoprimarydiamine to give the compound having the structure shown in the Summary of the Invention at (c).

This dinitrilodiamine is in itself sufficient as was previously noted to form coating materials or to undergo other reactions as noted in the Detailed Description of the Invention.

Carrying the reaction out further the dinitrolodiamine is further reduced with hydrogen pressure as previously described by utilizing 400 grams of the dinitrilodiamine, 59 grams of (62% solids) methanol wet Raney nickel blanketed in 26 grams of ammonia with the hydrogen gas introduced as required. The additional Raney nickel used to enhance the rate of reaction but may be omitted if the original Raney nickel is not filtered out of the reaction vessel. The mixture without the hydrogen gas present is stirred in a sealed reactor and heated to 60° C. at which time the hydrogen gas is added to bring the total pressure to 22,000 mm Hg while the temperature is gradually raised to 100° C. for the remainder of the hydrogenation. After one hour the hydrogenation is complete and the product is stripped of the solvent and ammonia. The tetram has a total amine number of 506.3, a primary amine number of 253.2 and a tertiary amine number of 132.2. The secondary amine number is obtained as the difference between the sum of the primary and tertiary amine number when subtracted from the total amine number.

The foregoing reaction to give the monotertiarymonosecondarydiprimarytetramine may be carried out with any of the foregoing variations previously listed with substantially similar results.

A particularily interesting variable of the present invention is the utilization of a mixture of primary amines derived from distilled soya sterol sludge. The composition of such a fatty portion ($R^1$) of the amine is 50% to 60% linoleic, 15% to 30% oleic, 5% to 15% linolenic, and 5% to 25% by weight of a mixture of palmitic and stearic acid fractions. A second tetram is prepared as above having 55%, 23%, 8%, and 14% respectively of the above listed fatty acids as $R^1$ substituents.

EXAMPLE II

The monotertiarymonosecondarydiprimarytetramine is used to prepare a tough, hard epoxy resin coating utilizing bisphenol A. The coating itself has a formulation of

| | |
|---|---|
| bisphenol A | 80 parts |
| Methyl isobutyl ketone | 3 parts |
| Methyl ethyl ketone | 5 parts |
| Toluene | 3 parts |
| Ethyl cellosolve | 9 parts |

A second mixture is made up containing 80% of the tetram of Example I with remainder of that solution being a normal butanol. The first mixture containing the epoxy resin is utilized at 16.67 parts with 7.84 parts of the tetram. A second coating is made up again using 16.67 parts of the epoxy resin and 8.22 parts of the distilled soya sterol residue tetram described in Example I.

Films were cast using a 3 mm doctor blade on glass and Black Plate panels using each of the coating mixtures. Both coatings were tack free following 24 hours and exhibited a Sward Rocker Hardness after 7 days at room temperature of 53 and 48 respectively, indicating that both coatings made in accordance with the present invention exhibited an extremely smooth surface.

What is claimed is:

1. A non-linear monotertiarymonosecondarydiprimarytetramine having the structural formula

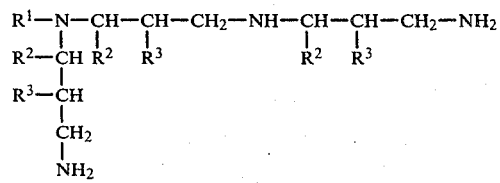

wherein R$^1$ is an organic moiety having from 4 to 40 carbon atoms and R$^2$ is selected from the group consisting of alkyl and alkenyl radicals having from 1 to 40 carbon atoms, hydrogen, phenyl, phenylalkyl and alkylphenyl derivatives and mixtures thereof, and R$^3$ is hydrogen or methyl and mixtures thereof.

2. The amine of claim 1 wherein R$^1$ is selected from the group consisting of alkyl and alkenyl radicals having from 10 to 22 carbon atoms.

3. The amine of claim 2 wherein R$^1$ has an even number of carbon atoms from 12 to 18.

4. The amine of claim 1 wherein R$^2$ is selected from the group consisting of phenyl and alkylphenyl radicals and mixtures thereof.

5. The amine of claim 1 wherein R$^1$ is selected from the group consisting of alkylphenyls and phenylalkyls and mixtures thereof.

6. The amine of claim 1 wherein R$^2$ is selected from the group consisting of alkyl and alkenyl radicals having from 1 to 4 carbon atoms.

7. The amine of claim 1 wherein R$^3$ is methyl.

8. The amine of claim 1 wherein R$^2$ is hydrogen.

9. The amine of claim 1 wherein R$^3$ is hydrogen.

10. The amine of claim 1 wherein R$^2$ and R$^3$ are hydrogen.

11. A process for the production of a non-linear monotertiarymonosecondarydiprimarytetramine including the steps of (a) reacting a primary amine of the formula

R$^1$NH$_2$ wherein R$^1$ is an organic moiety having from 4 to 40 carbon atoms with a nitrile of the formula

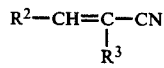

wherein R$^2$ is selected from the group consisting of alkyl and alkenyl radicals having from 1 to 40 carbon atoms, hydrogen, phenyl, phenylalkyl, alkylphenyl derivatives and mixtures thereof; and R$^3$ is hydrogen or methyl or mixtures thereof; and R$^3$ is hydrogen or methyl or mixtures thereof to yield

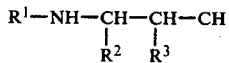

(b) reducing the compound prepared in (a) with hydrogen to form a compound of the formula

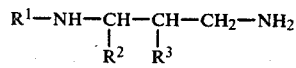

wherein R$^1$, R$^2$, and R$^3$ are defined above;

(c) then reacting the reduced compound of (b) with a second portion of a nitrile described in (a) to form

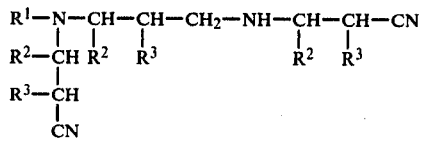

(d) then reducing the compound described in (c) with hydrogen to form

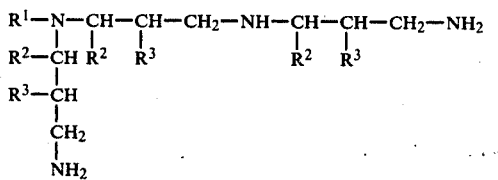

wherein R$^1$, R$^2$, and R$^3$ are as defined above whereby the process is conducted utilizing a hydrogenation catalyst in the hydrogenation steps and water is not present at any substantial level during the hydrogenation steps.

12. The process of claim 11 wherein R$^1$ is an aliphatic radical.

13. The process of claim 12 wherein R$^1$ is an alkyl radical.

14. The process of claim 12 wherein R$^1$ is an alkenyl radical.

15. The process of claim 11 wherein R$^1$ is selected from the group consisting of alkylphenyl and phenylalkyl radicals.

16. The process of claim 12 wherein R$^1$ has from 10 to 22 carbon atoms.

17. The process of claim 16 wherein R$^1$ has an even number of carbon atoms from 12 to 18.

18. The process of claim 11 wherein R$^2$ is hydrogen.

19. The process of claim 11 wherein R$^2$ is selected from the group consisting of alkyl and alkenyl radicals having from 1 to 4 carbon atoms.

20. The process of claim 19 wherein R$^2$ is selected from the group consisting of methyl and ethyl radicals.

21. The process of claim 11 wherein R$^3$ is hydrogen.

22. The process of claim 11 wherein R$^3$ is methyl.

23. The process of claim 11 wherein R$^2$ and R$^3$ are hydrogen.

24. The process of claim 11 wherein steps (b) and (d) are carried out in the presence of ammonia with the hydrogen absolute pressure of not less than 15,000 mm Hg at a temperature of from about 60° C. to about 120° C.

* * * * *

UNITED STATES PATENT AND TRADEMARK OFFICE
CERTIFICATE OF CORRECTION

PATENT NO. : 4,257,984
DATED : March 24, 1981
INVENTOR(S) : Stuart A. Harrison

It is certified that error appears in the above-identified patent and that said Letters Patent are hereby corrected as shown below:

In claim 11, beginning at line 43, after "derivatives and mixtures thereof;", delete "and $R^3$ is hydrogen or methyl or mixtures thereof;".

In claim 11, the formula after "yield", at line 45, reading:

should read:

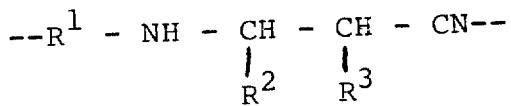

Signed and Sealed this

Twenty-sixth Day of February 1985

[SEAL]

Attest:

DONALD J. QUIGG

Attesting Officer

Acting Commissioner of Patents and Trademarks